US008630476B2

(12) United States Patent
Okada et al.

(10) Patent No.: US 8,630,476 B2
(45) Date of Patent: Jan. 14, 2014

(54) SYSTEM AND METHOD FOR SUPPORTING DISCOVERY OF DEFECT INCLUDED IN INSPECTION SUBJECT (75) Inventors: Masakuni Okada, Tokyo (JP); Yumi Mori, Tokyo (JP); Munehiro Doi, Tokyo (JP); Shinsuke Ueyama, Tokyo (JP)

(73) Assignee: International Business Machines Corporation, Armonk, NY (US)

( * ) Notice: Subject to any disclaimer, the term of this patent is extended or adjusted under 35 U.S.C. 154(b) by 433 days.

(21) Appl. No.: 13/020,227

(22) Filed: Feb. 3, 2011

(65) Prior Publication Data

US 2011/0123094 A1 May 26, 2011

(30) Foreign Application Priority Data

Sep. 18, 2008 (JP) ................................. 2008-239073

(51) Int. Cl.
*G06K 9/00* (2006.01)
(52) U.S. Cl.
USPC ......................................................... 382/141
(58) Field of Classification Search
None
See application file for complete search history.

(56) References Cited

U.S. PATENT DOCUMENTS

| 6,721,391 | B2 | | 4/2004 | McClelland et al. |
| 6,973,209 | B2 | * | 12/2005 | Tanaka ........................... 382/149 |
| 7,388,979 | B2 | * | 6/2008 | Sakai et al. .................... 382/149 |
| 2004/0228515 | A1 | * | 11/2004 | Okabe et al. ................... 382/145 |
| 2005/0254699 | A1 | * | 11/2005 | Sano et al. ..................... 382/149 |
| 2005/0271261 | A1 | * | 12/2005 | Onishi et al. .................. 382/149 |

FOREIGN PATENT DOCUMENTS

| CN | 1392999 | 1/2003 |
| CN | 101113958 | 1/2008 |
| JP | 10504905 | 5/1998 |
| JP | 11258178 | 9/1999 |
| JP | 2000197035 | 7/2000 |
| JP | 2000356512 | 12/2000 |
| JP | 2004226328 | 8/2004 |
| JP | 2005303269 | 10/2005 |
| JP | 2006171816 | 6/2006 |
| JP | 2006322774 | 11/2006 |
| JP | 2007-085995 | 5/2007 |
| JP | 200865555 | 3/2008 |
| JP | 200028547 | 3/2011 |
| WO | 0223480 | 3/2002 |
| WO | 2010/032562 A1 | 3/2010 |

OTHER PUBLICATIONS

International Search Report dated Mar. 8, 2009.
"Embedded Surface Damage Detection Technology of Bridge Cable", Guo Yongcai, et al., Dec. 21, 2006; China Academic Journal Electronic Publishing House.

* cited by examiner

*Primary Examiner* — Vikkram Bali
(74) *Attorney, Agent, or Firm* — Katherine S. Brown (57) ABSTRACT

A system, and methods of operation thereof, is presented that permits determination of a defect in an inspection subject by means of processing an image of said inspection subject, which system avoids exhaustion of bandwidth in a communication line connected to the image processing unit. The system includes a unit to receive an image, a transmission queue and a buffer to store the image, an image processing unit to determine whether the image includes a defect image, a unit that generates defect information when the presence of a defect image is determined, an image extraction unit that extracts the defect image based on the defect information, and a storage unit for storing such defect image.

12 Claims, 10 Drawing Sheets

| | |
|---|---|
| CAPTURE IMAGE ID : | #5 |
| NUMBER OF DEFECT AREAS : | 3 |
| DEFECT AREA INFORMATION #1 : | |
|     top-left : | (10, 20) |
|     width : | 35 |
|     height : | 60 |
| DEFECT AREA INFORMATION #2 : | |
|     top-left : | (28, 40) |
|     width : | 40 |
|     height : | 70 |
| DEFECT AREA INFORMATION #3 : | |
|     top-left : | (110, 205) |
|     width : | 112 |
|     height : | 160 |

SYSTEM AND METHOD FOR SUPPORTING DISCOVERY OF DEFECT INCLUDED IN INSPECTION SUBJECT

This application claims priority to Japanese application number 2008-239073, filed Sep. 18, 2008 and to PCT application JP2009/063730 filed Aug. 3, 2009, both entitled "System and Method for Supporting Discovery of Defect Included in Inspection Subject".

TECHNICAL FIELD

The present invention relates to a system and a method for supporting discovery of a defect included in an inspection subject. In particular, the invention relates to a system and a method for supporting discovery of a defect included in an inspection subject by processing an image of the inspection subject.

RELATED ART

In recent years, defects included in manufactured liquid crystal displays (LCDs), wafers, or the like have been discovered automatically in the production line of a plant for manufacturing semiconductor wafers or the like by photographing surfaces of the LCDs, wafers, or the like using a high-resolution camera and then analyzing obtained image data.

As a technology for discovering defects included in minute patterns of photomasks or the like used when manufacturing LCDs, there has been proposed a technology for outputting a result obtained by comparing an optical image of a photomask and a reference image generated from graphics data included in a CAD (computer-aided design) data file (for example, see Japanese Unexamined Patent Application Publication No. 2007-85995 "Patent Document 1"). In Patent Document 1, an optical image acquisition unit acquires an optical image of a photomask that is formed by drawing a graphics represented by graphical data included in a CAD data file and serves as a sample. Subsequently, a comparison circuit compares the optical image and a reference image generated by converting the graphical data included in the CAD data file into image data and then subjecting the image data to a predetermined filtering process, using a predetermined algorithm. If the comparison circuit determines that the optical image has a defect, it outputs the optical image to a review apparatus.

As described above, there has existed the technology for discovering defects included in LCDs or the like by processing images of the LCDs or the like. Incidentally, with recent, considerable upsizing of the inspection areas of LCDs or the like as well as recent increases in resolution of LCDs or the like for the purpose of displaying a large amount of data, higher performance has been required with respect to image processing for comparing an optical image and a reference image. For this reason, it is considered to use a high-function, dedicated unit different from an optical image unit apparatus for acquiring an optical image as the comparison circuit for comparing an optical image and a reference image described in Patent Document 1. However, even if the performance requirement with respect to image processing is satisfied by using such a high-function, dedicated unit, there remains a problem that when outputting an image, which has been determined as having a defect, to a review apparatus, the bandwidth used when communicating data within a system is exhausted due to considerable increases in amount of data transmission. The bandwidth here refers to the capacity of a transmission line and is represented by a bit rate at which data can be transmitted.

Even if a system configuration allowing ensuring a maximum of bandwidth is adopted so as to resolve the above-mentioned problem, the capability of the comparison circuit to communicate with peripheral units may not keep up with increases in amount of data transmission, since the comparison circuit must concentrate on processing images.

Also, it is considered to compress an image determined as having a defect in order to reduce the amount of data transmission. However, there occurs another problem that this process reduces the original image processing performance.

Accordingly, an object of the present invention is to avoid exhaustion of the bandwidth of a communication line connected to a unit for performing image processing in which whether a photographic image of an inspection subject includes an image of a defective portion of the inspection subject is determined. In other words, the object of the present invention is to avoid an increase in bandwidth of a communication line coupling an image processing unit and a result storage unit.

SUMMARY OF THE INVENTION

With the above-mentioned object, the present invention provides a system for supporting discovery of a defect included in an inspection subject. The system includes: an acquisition unit for acquiring a photographic image obtained by photographing the inspection subject; a determination unit coupled to the acquisition unit via a first communication line and intended to determine whether the photographic image obtained by the acquisition unit includes a defect image that is an image of an area including a defective portion of the inspection subject; and a storage unit coupled to the acquisition unit via a second communication line and intended to, if the determination unit determines that the photographic image includes the defect image, store the defect image. The acquisition unit transmits the photographic image to the determination unit via the first communication line as well as stores the photographic image in a memory thereof, and if the determination unit determines that the photographic image includes the defect image, the acquisition unit receives image identification information for identifying the defect image from the determination unit via the first communication line and transmits the defect image that is included in the photographic image stored in the memory and is identified by the image identification information, to the storage unit via the second communication line.

In this case, the image identification information may include at least one of an identification number of the photographic image, a number of the defective portions, and defect area information including a coordinate and an area of the defective portion.

Also, the acquisition unit may cut off the defect image from the photographic image stored in the memory and may transmit the cut-off defect image to the storage unit. In this case, if the acquisition unit receives, as the image identification information, area identification information for identifying an area occupied by the defect image in the photographic image stored in the memory, the acquisition unit may cut off, as the defect image, an area identified by the area identification information from the photographic image.

Also, if the acquisition unit receives, from the determination unit, information indicating that the photographic image stored in the memory does not include the defect image, the acquisition unit may delete the photographic image from the memory.

Also, the photographic image may include a plurality of fragments, and if the determination unit determines that at least one of the fragments included in the photographic image includes the defect image, the acquisition unit may transmit, to the storage unit, the at least one fragment including the defect image among the fragments included in the photographic image stored in the memory. In this case, if the acquisition unit receives, as the image identification information, fragment identification information for identifying the fragment including the defect image among the fragments included in the photographic image stored in the memory, from the determination unit, the acquisition unit may transmit the at least one fragment identified by the fragment identification information among the fragments, to the storage unit.

Also, the photographic image may include a plurality of fragments, and if the acquisition unit receives, from the determination unit, information indicating that a particular fragment among the fragments included in the photographic image stored in the memory does not include the defect image, the acquisition unit may delete the particular fragment from the memory.

Also, if the determination unit determines that the photographic image includes the defect image, the determination unit may delete the defect image without transmitting the defect image to the acquisition unit.

Also, the second communication line may be larger in bandwidth than the first communication line.

Also, the present invention provides a method for supporting discovery of a defect included in an inspection subject. The method includes the steps of: acquiring, from a photographing unit, a photographic image obtained by photographing the inspection subject using the photographing unit, by using an acquisition unit; transmitting the photographic image to a determination unit via a first communication line by using the acquisition unit; storing the photographic image in a memory of the acquisition unit by using the acquisition unit; determining whether the photographic image received from the acquisition unit via the first communication line includes a defect image that is an image of an area including a defective portion of the inspection subject, by using the determination unit; if the determination unit determines that the photographic image includes the defect image, transmitting image identification information for identifying the defect image to the acquisition unit via the first communication line, by using the determination unit; and transmitting the defect image that is included in the photographic image stored in the memory and is identified by the image identification information, to a storage unit via the second communication line by using the acquisition unit.

Also, the present invention provides another method for supporting discovery of a defect included in an inspection subject. The method includes the steps of: acquiring, from a photographing unit, a plurality of fragments of a photographic image obtained by photographing the inspection subject using the photographing unit, by using an acquisition unit; transmitting the fragments to a determination unit via a first communication line by using the acquisition unit; storing the fragments in a memory of the acquisition unit by using the acquisition unit; determining whether at least one of the fragments received from the acquisition unit via the first communication line includes a defect image that is an image of an area including a defective portion of the inspection subject, by using the determination unit; if the determination unit determines that at least one of the fragments includes the defect image, transmitting fragment identification information for identifying the at least one fragment including the defect image among the fragments stored in the memory and area identification information for identifying an area occupied by the at least one defect image in the fragment to the acquisition unit via the first communication line, by using the determination unit; cutting off, as the defect image, an area that is included in the at least one fragment identified by the fragment identification information among the fragments stored in the memory and is identified by the area identification information, by using the acquisition unit; and transmitting the cut-off defect image to a storage unit by using the acquisition unit.

By adopting the present invention, there is avoided exhaustion of the bandwidth of a communication line connected to a unit for performing image processing in which whether a photographic image of an inspection subject includes an image of a defective portion of the inspection subject is determined.

REFERENCE NUMERAL

10: camera
20: capture unit
21: reception unit
22: transmission queue
23: transmission/reception unit
24: buffer
25: image extraction unit
26: transmission unit
30: image processing unit
31: transmission/reception unit
32: buffer
33: image analysis unit
34: defect information generation unit

DESCRIPTION OF EMBODIMENTS

The mode (hereafter referred to as an "embodiment") for carrying out the present invention will be described in detail with reference to the accompanying drawings.

Figure 1:
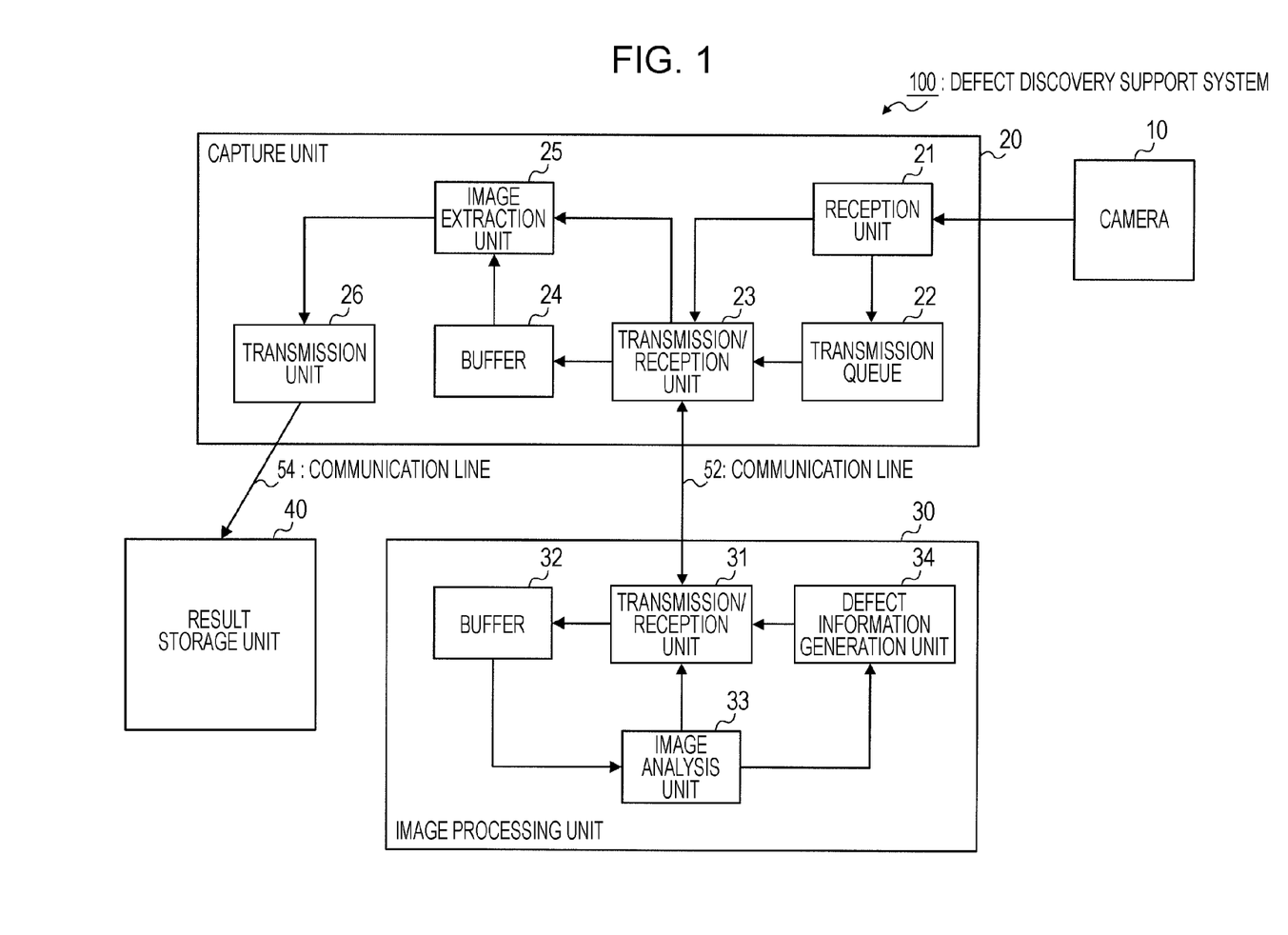
FIG. 1 is a block diagram showing a functional configuration of a defect discovery support system according to an embodiment of the present invention.

First, a defect discovery support system according to this embodiment will be described using an LCD as an example of an inspection subject. FIG. 1 is an overall configuration example of a defect discovery support system 100. As shown in FIG. 1, the defect discovery support system 100 includes a camera 10, a capture unit 20, an image processing unit 30, and a result storage unit 40.

The camera 10 is preferably a high-performance area scan camera or line scan camera. The capture unit 20 and result storage unit 40 may be each realized, for example, by a server. The image processing unit 30 may be realized by a blade server including a multi-core CPU. In FIG. 1, the camera 10 is represented by one box; however, if the inspection area of an LCD or the like is large, multiple cameras 10 are preferably provided so that small areas of a surface of the LCD or the like are photographed by the cameras. In this case, multiple capture units 20 corresponding to the multiple cameras 10 are preferably provided.

The capture unit 20 and image processing unit 30 are coupled via a communication line 52. The capture unit 20 and result storage unit 40 are coupled via a communication line 54. The coupling via the communication line 52 or communication line 54 is realized, for example, by the Ethernet (registered trademark) using an Ethernet (registered trademark) switch, the InfiniBand using an IB switch, or PCIe using a PCIe bridge. The communication line 52 is an example of a first communication line and the communication line 54 is an example of a second communication line. A bandwidth larger than that of the first communication line is set for the second communication line.

Hereafter, the functions of the units included in the defect discovery support system 100 will be described.

The camera 10 photographs a lighting display screen of an LCD. Specifically, when an LCD, which is an inspection subject, comes along the manufacturing process line, the camera 10 photographs a predetermined screen area on the LCD. In this case, the lighting display screen may include various test patterns for discovering a defect. Subsequently, image data obtained from the photographing is transmitted to the capture unit 20 one after another.

The capture unit 20 is an example of an acquisition unit for acquiring an image and includes a reception unit 21, a transmission queue 22, a transmission/reception unit 23, an image extraction unit 25, and a transmission unit 26.

The reception unit 21 receives image data obtained by photographing performed by the camera 10 one after another.

The transmission queue 22 stores the image data (hereafter referred to as "capture image") received by the reception unit 21 until the capture image is transmitted to the image processing unit 30. The capture image here is an example of a photographic image obtained by photographing an inspection subject.

The transmission/reception unit 23 transmits the capture image stored in the transmission queue 22 to the image processing unit 30 or receives, from the image processing unit 30, information indicating in which capture image a defect has been discovered and indicating the position in which the defect has been discovered in the capture image or information indicating the size of the defect (these types of information will be referred to as "defect information").

The buffer 24 retains a given amount of capture images even after the capture images are transmitted to the image processing unit 30.

The image extraction unit 25 extracts image data indicating an area including a defective portion (hereafter referred to as a "defect image") from the capture image retained in the buffer 24, on the basis of defect information received by the transmission/reception unit 23.

The transmission unit 26 transmits the defect image extracted by the image extraction unit 25 to the result storage unit 40.

The image processing unit 30 is an example of a determination unit for determining whether a capture image includes a defect image, and includes a transmission/reception unit 31, a buffer 32, an image analysis unit 33, and a defect information generation unit 34.

The transmission/reception unit 31 receives a capture image from the capture unit 20. If no defect is found in the capture image, the transmission/reception unit 31 provides notification to that effect to the capture unit 20. If a defect is found, the transmission/reception unit 31 transmits defect information to the capture unit 20.

The buffer 32 stores the capture image received by the transmission/reception unit 31 from the capture unit 20. This capture image is deleted after image processing including analysis of the image and generation of defect information is completed.

The image analysis unit 33 analyzes the capture image stored in the buffer 32 to determine whether the capture image has a defect. If there is a defect, the image analysis unit 33 analyzes and determines the position and size (shape, area, etc.) of the defect.

The defect information generation unit 34 generates defect information if the image analysis unit 33 determines that the capture image has a defect. Note that the defect information is not image data indicating the defective portion but information for identifying the defective portion. The amount of data included in the defect information is smaller than the amount of image data. This point will be described in detail later.

The result storage unit 40 is an example of a storage unit for receiving a transmitted defect image and stores a defect image received from the capture unit 20. For example, the result storage unit 40 is a file server including a hard disk drive (HDD) for storing a defect image.

Next, operations of the defect discovery support system 100 according to this embodiment will be schematically described.

FIGS. 2 to 5 are drawings showing the operations in the time series. Note that among the elements of the capture unit 20 and image processing unit 30 shown in FIG. 1, only elements necessary for the description are shown in these drawings.

Figure 2:
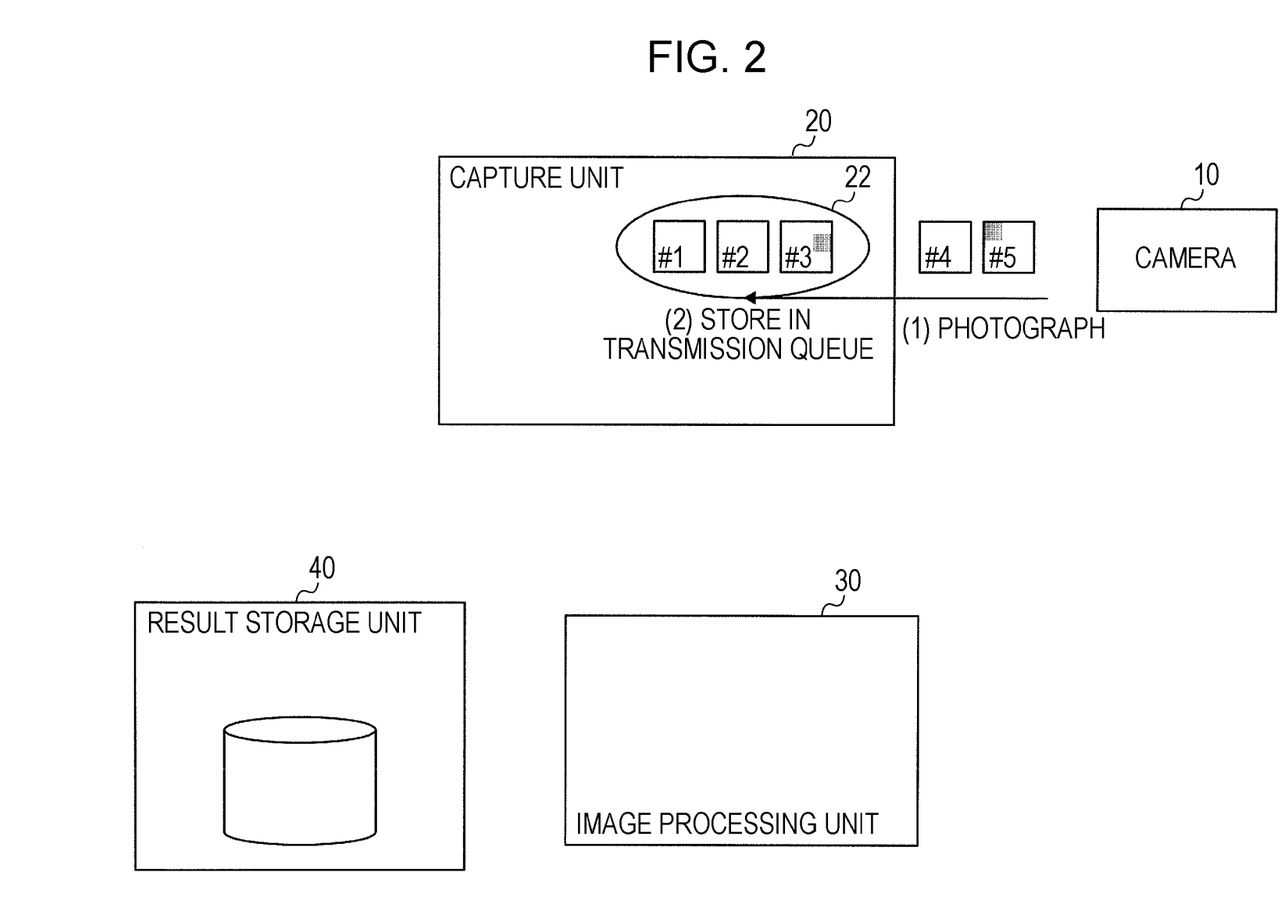
FIG. 2 is a drawing schematically showing operations performed when a capture unit according to this embodiment stores a capture image in a transmission queue.

FIG. 2 is a drawing schematically showing operations performed when the capture unit 20 stores, in the transmission queue 22, image data obtained by photographing performed by the camera 10.

First, the camera 10 photographs an LCD, which is an inspection subject, and transmits image data obtained from the photographing, to the capture unit 20 one after another (1).

Next, the capture unit 20 stores the capture image received from the camera 10 in the transmission queue 22 (2). The capture image is assigned a "capture image ID" for uniquely identifying the capture image. Hereafter, a capture image having a capture image ID "N" will be represented by a "capture image #N." In FIG. 2, first, capture images #1 to #3 are stored and, then, capture images #4 and #5 are transmitted from the camera 10. Hatches in a capture image represent a defective portion. This portion will be recognized as a defect in a later image analysis.

Figure 3:
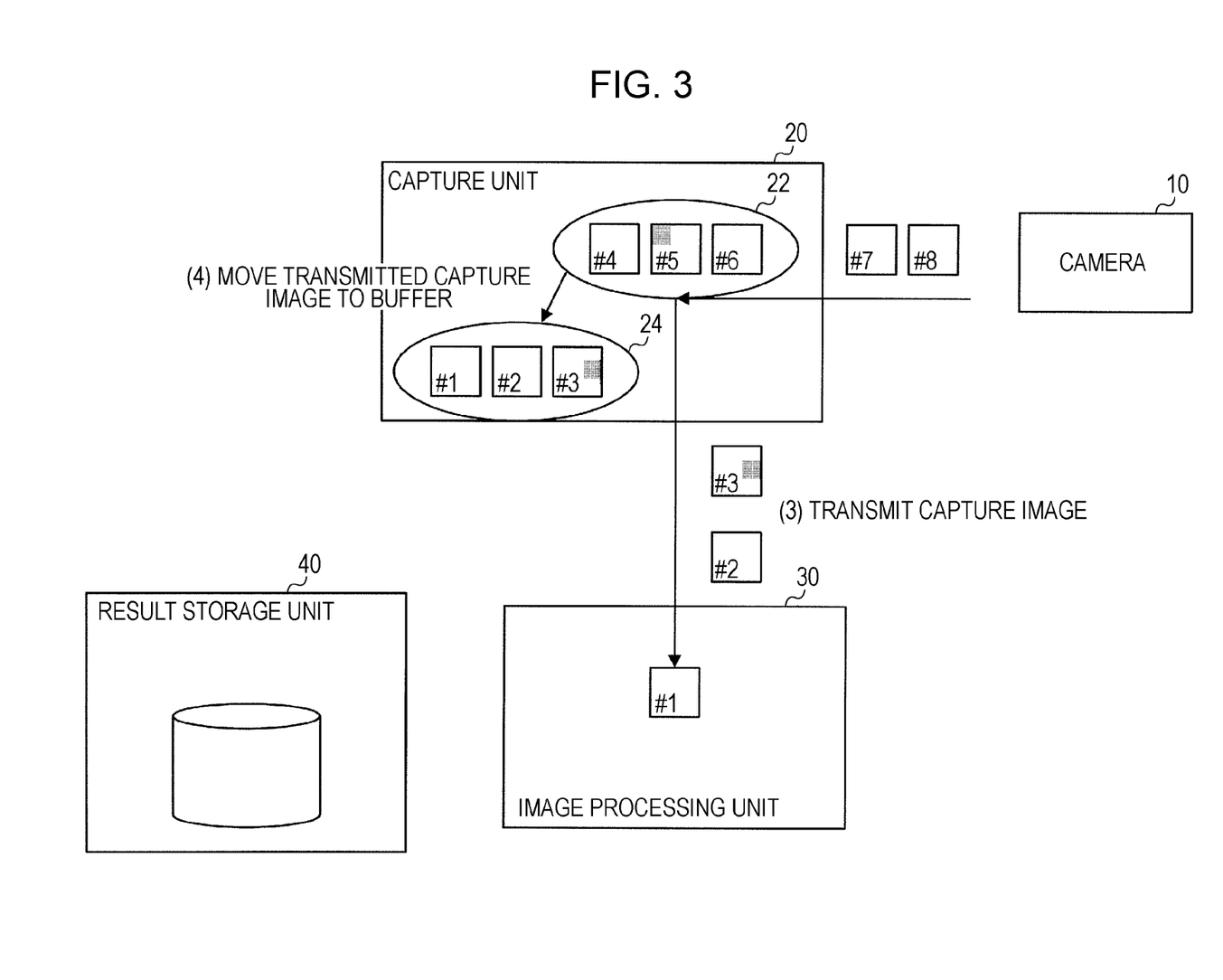
FIG. 3 is a drawing schematically showing operations performed when the capture unit according to this embodiment transmits capture images to an image processing unit.

FIG. 3 is a drawing schematically showing operations performed when the capture unit 20 transmits capture images to the image processing unit 30.

First, the capture unit 20 transmits the capture images stored in the transmission queue 22 to the image processing unit 30 (3). In FIG. 3, a state is shown in which the capture images #1 to #3, which are stored in the transmission queue 22 in FIG. 2, are being transmitted to the image processing unit 30. Subsequently, new capture images #4 to #8 are transmitted from the camera 10 and, among these, the capture images #4 to #6 are stored in the transmission queue 22.

Subsequently, the capture unit 20 moves the capture images, which have been already transmitted to the image processing unit 30, to the buffer 24 (4). Specifically, the capture images #1 to #3, which have been transmitted to the image processing unit 30, are moved to the buffer 24. This means that the capture unit 20 and image processing unit 30 have the same capture images temporarily.

Figure 4:
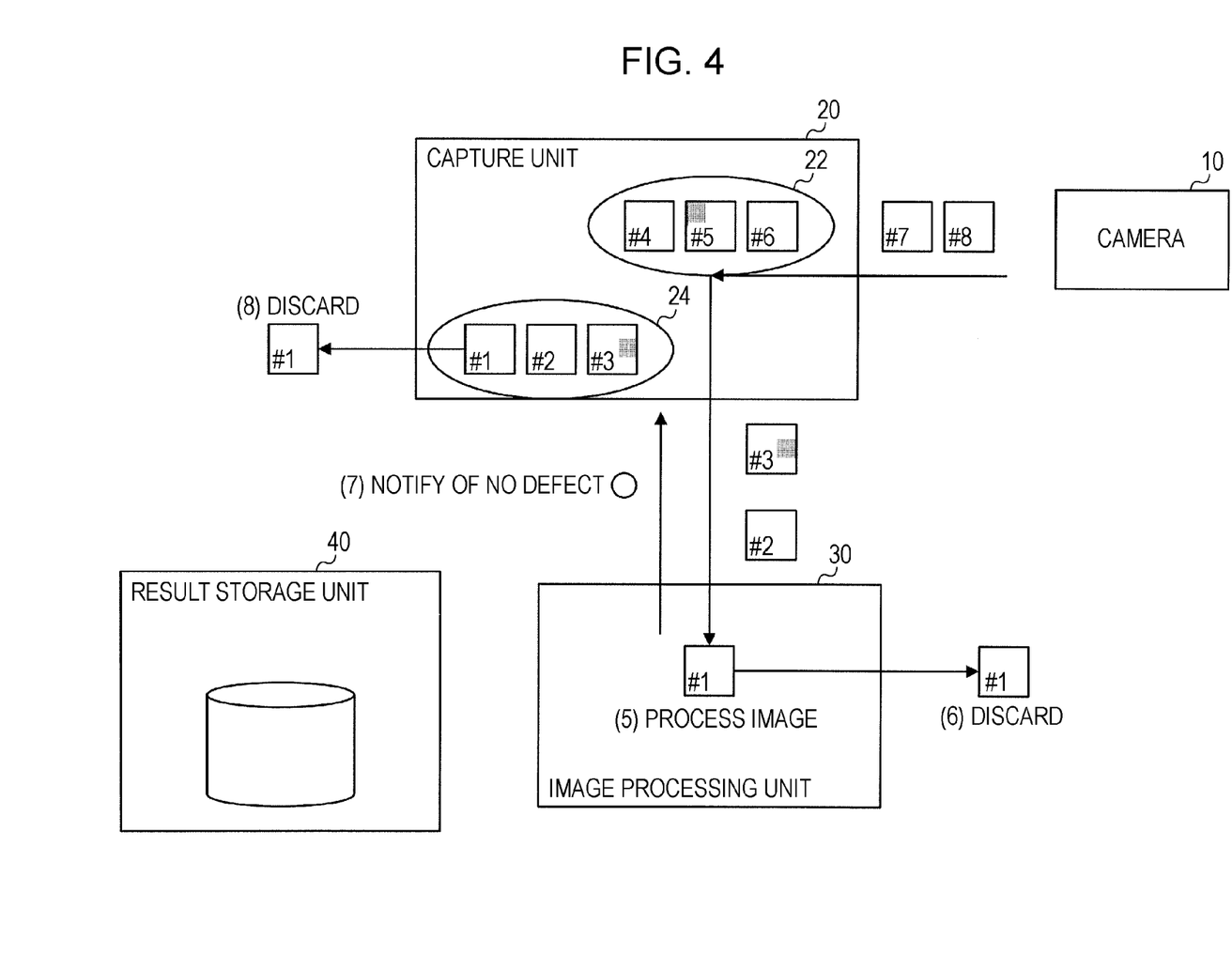
FIG. 4 is a drawing schematically showing operations performed when the image processing unit according to this embodiment notifies the capture unit that there is no defect.

FIG. 4 is a drawing schematically showing operations performed when the image processing unit 30 determines that there is no defect after performing image processing. First, the image processing unit 30 processes the capture image #1 among the capture images transmitted in FIG. 3 and then determines that there is no defect (5). Subsequently, the image processing unit 30 discards the processed capture image #1 (6). Subsequently, the image processing unit 30 notifies the capture unit 20 that the capture image #1 has no defect (7). Finally, the capture unit 20 discards the capture image #1 retained in the buffer 24 (8).

Figure 5:
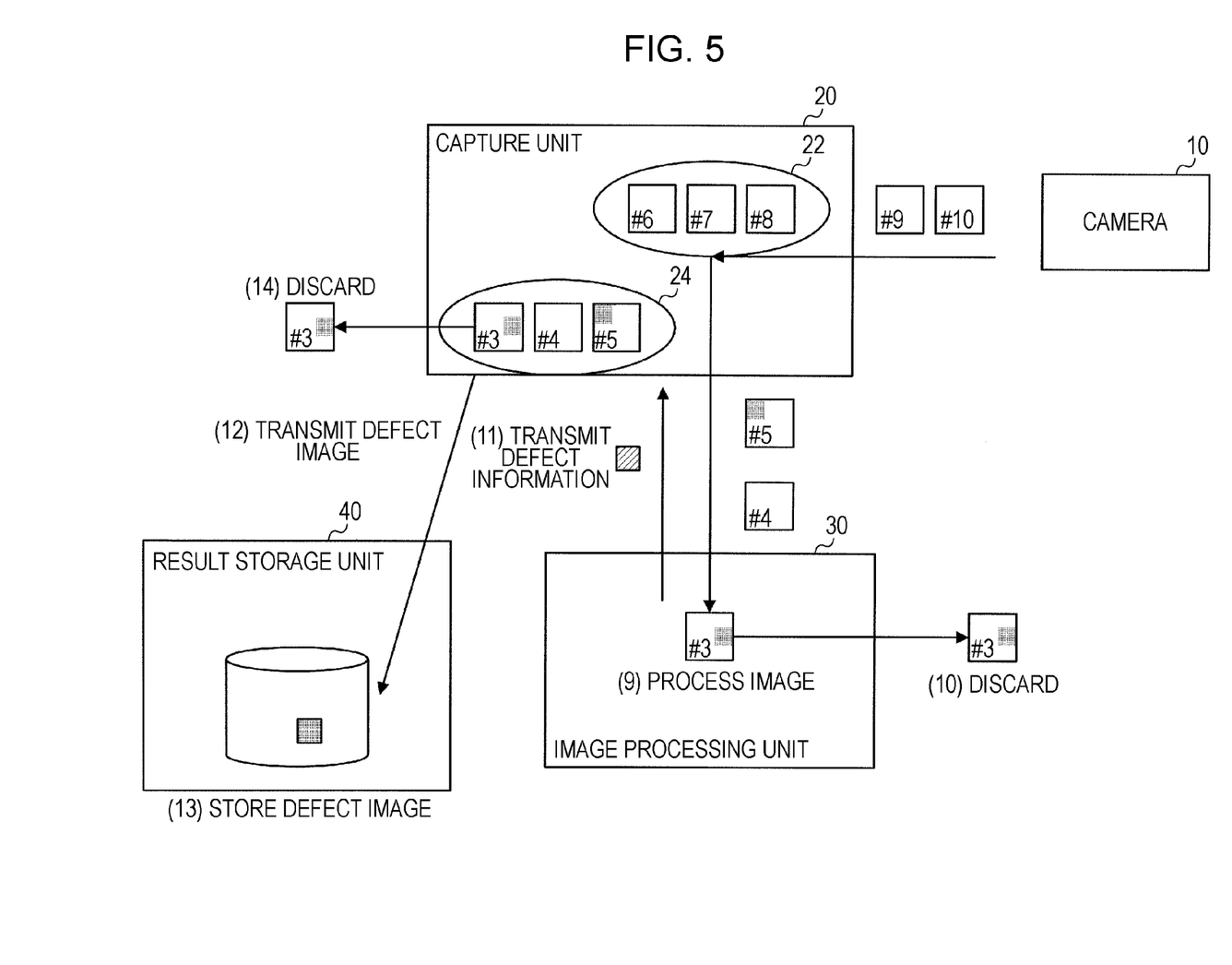
FIG. 5 is a drawing schematically showing operations performed when the image processing unit according to this embodiment transmits defect information to the capture unit.

FIG. 5 is a drawing schematically showing operations performed when the image processing unit 30 determines that there is a defect after performing image processing. First, the image processing unit 30 processes the capture image #3 among the capture images transmitted in FIG. 3 and then discovers that there is a defect (9). Subsequently, the image processing unit 30 discards the processed capture image #3 (10). That is, even if there is a defect, the capture image is discarded like in a case where there is no defect.

Subsequently, the image processing unit 30 transmits defect information to the capture unit 20 (11). The defect information here is not a defect image itself but data including information for identifying the position and size of a defect image included in the capture image. Therefore, the amount of data included in the defect information is smaller than that included in the defect image. Subsequently, the capture unit 20 extracts the defect image from the capture image #3 stored in the buffer 24 and transmits the defect image to the result storage unit 40 (12). The result storage unit 40 stores the defect image (13).

Finally, the capture unit 20 discards the processed capture image #3, that is, the capture unit 20 discards the capture image #3 from which the defect image has been extracted (14).

Hereafter, the defect information transmitted from the image processing unit 30 to the capture unit 20 in FIG. 5 will be described.

Figure 6:
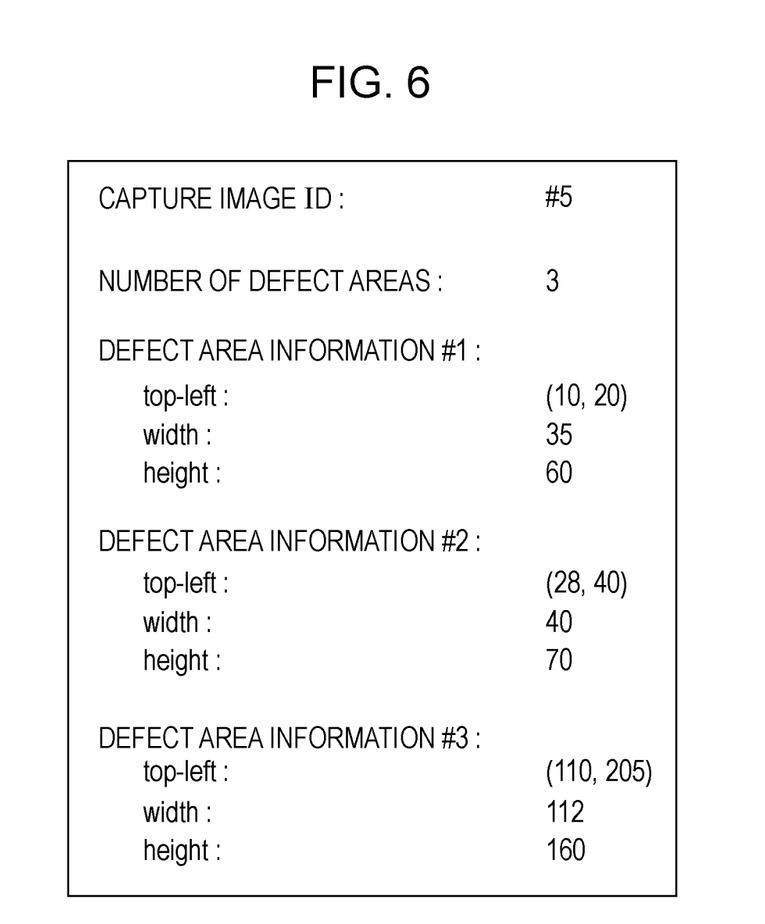
FIG. 6 is a drawing showing a specific example of defect information generated in this embodiment.

FIG. 6 is a drawing showing a specific example of defect information. As described above, defect information is not image data itself but data including information as described below and having a data size smaller than that of image data. In this embodiment, defect information is used as an example of image identification information for identifying a defect image. As shown in FIG. 6, the defect information includes a capture image ID, the number of defect areas, and defect area information.

As described above, a capture image ID is identification information for uniquely identifying a capture image. A capture image ID is assigned to each of capture images obtained by photographing areas obtained by dividing the screen of an LCD. For example, if four capture images are obtained by dividing the screen of an LCD into four parts, the four capture images are assigned capture images IDs such as #5, #6, #7, and #8. FIG. 6 shows the case of the capture image #5. In this embodiment, a capture image ID is used as an example of fragment identification information for identifying a fragment of an image.

The number of defect areas refers to the number of defect areas discovered in a capture image. Multiple defects may be included in one capture image. In such a case, rectangular areas each including a defect are defined as defect areas. In FIG. 6, a case where three defect areas have been discovered in the capture image #5 is shown.

Defect area information refers to information for identifying each of areas corresponding to the number of defect areas and includes the following information items. One of the items is "top-left." This indicates the coordinates of the top-left corner of a defect area in a case where the top-left corner point of a capture image is used as the origin. Another item is "width" which refers to the width of the defect area. Yet another item is "height" which refers to the height of the defect area. Since the number of defect areas is "3," the defect information includes three pieces of defect area information. In this embodiment, defect area information is provided as an example of area identification information for identifying an area occupied by a defect image. While the coordinates, width, and height are used as area identification information in this embodiment, any information may be used as long as the information allows identification of an area. For example, the coordinates of the top-left corner point and the coordinates of the right-bottom point, or the like may be used.

Also, this defect information may include information indicating the severity of a defective portion obtained by analyzing the density of an image of the defective portion or information indicating the size (area) of the defective portion.

Hereafter, operations of the defect discovery support system 100 according to this embodiment will be described in detail. See also FIG. 1.

Figure 7:
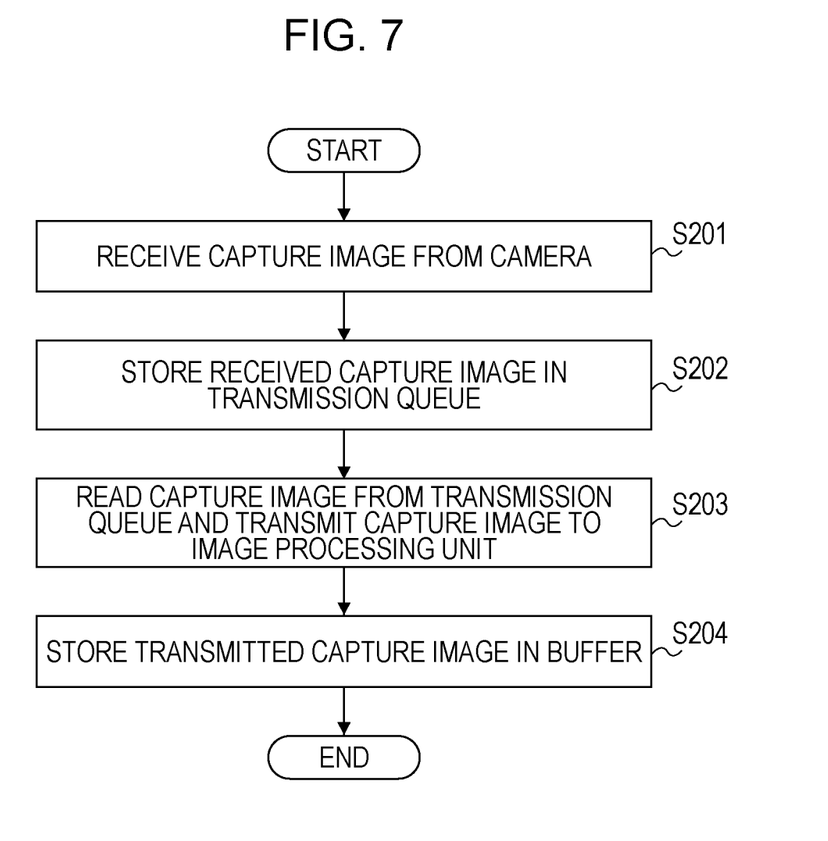
FIG. 7 is a flowchart showing an example of operations performed when the capture unit according to this embodiment transmits a capture image to the image processing unit.

FIG. 7 is a flowchart showing example operations of the capture unit 20 from the reception of a capture image from the camera 10 to the transmission of the capture image to the image processing unit 30. In the capture unit 20, first, the reception unit 21 receives a capture image from the camera 10 (step S201). Then, the reception unit 21 stores the received capture image in the transmission queue 22 (step 202).

Subsequently, the reception unit 21 notifies the transmission/reception unit 23 that the capture image has been stored in the transmission queue 22. The transmission/reception unit 23 reads the capture image from the transmission queue 22 and transmits the capture image to the image processing unit 30 (step 203). Also, the transmission/reception unit 23 stores the capture image, which has been transmitted, in the buffer 24 (step 204).

In these example operations, once the capture image transmitted from the camera 10 has been stored in the transmission queue 22, the transmission/reception unit 23 extracts the capture image and transmits the capture image to the image processing unit 30. However, without synchronizing with the storage of a capture image transmitted from the camera 10 in the transmission queue 22, the transmission/reception unit 23 may read out the capture image and transmit the capture image to the image processing unit 30. For example, the transmission/reception unit 23 may check whether a capture image is stored in the transmission queue 22, at given intervals and if a capture image is stored, the transmission/reception unit 23 may read out the capture image and transmit it to the image processing unit 30.

Figure 8:
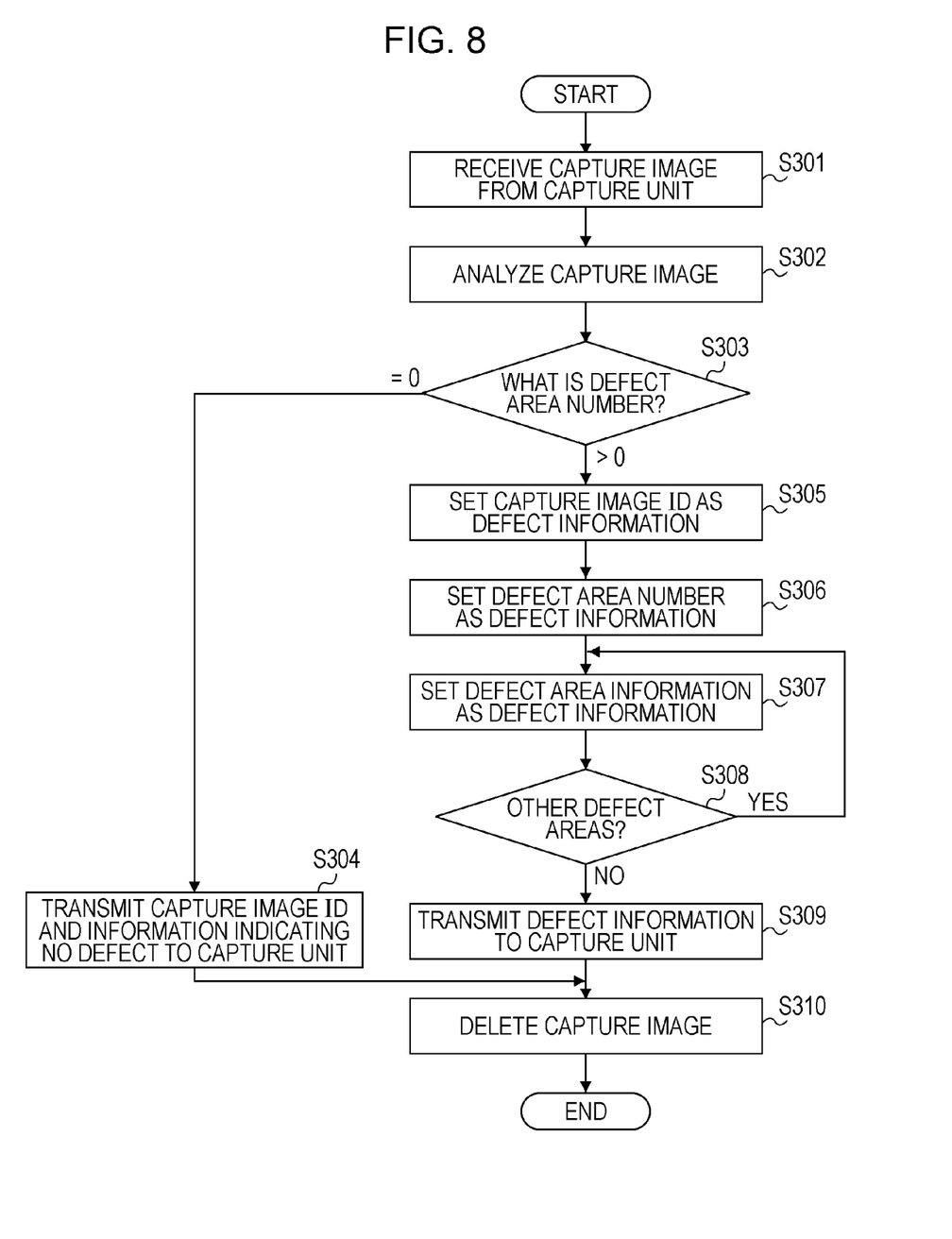
FIG. 8 is a flowchart showing an example of operations performed when the image processing unit analyzes an image.

FIG. 8 is a flowchart showing an example of operations performed by the image processing unit 30 that has received a capture image. In the image processing unit 30, first, the transmission/reception unit 31 receives a capture image and stores the received capture image in the buffer 32 (step 301).

Subsequently, the image analysis unit 33 analyzes the capture image stored in the buffer 32 (step 302). Specifically, the image analysis unit 33 compares the capture image and a reference image indicating a correct pattern of an LCD area corresponding to the capture image. For example, if a predetermined LCD area is photographed by the camera 10, identification information of the camera 10 is transmitted to the capture unit 20 together with image data obtained by the photographing. Subsequently, the LCD area corresponding to the capture image may be identified on the basis of the identification information of the camera 10, and a reference image indicating a correct pattern of this area may be read out from a reference image storage unit (not shown). Subsequently, the image analysis unit 33 obtains the number of areas that are small areas included in the capture image and are different in pattern from corresponding areas in the reference image, as well as obtains the positions and sizes of such areas.

Subsequently, the image analysis unit 33 determines whether the number of defect areas is "0" (step 303). That is, the image analysis unit 33 determines whether the capture image has no defect.

If the image analysis unit 33 determines that the number of defect areas is "0," it provides notification to that effect to the transmission/reception unit 31. The transmission/reception unit 31 transmits a capture image ID corresponding to the capture image and information indicating that there is no defect, to the capture unit 20 (step 304). Subsequently, the transmission/reception unit 31 deletes the capture image corresponding to the capture image ID from the buffer 32 (step 310).

In contrast, if the image analysis unit 33 determines that the number of defect areas is not "0," it notifies the defect information generation unit 34 of a capture image ID corresponding to the capture image, the number of defect areas, and the positions and sizes of the defect areas. The defect information generation unit 34 generates defect information. Specifically, the defect information generation unit 34 sets the capture image ID as defect information (step 305). Subsequently, the defect information generation unit 34 sets the number of defect areas as defect information (step 306). Subsequently, the defect information generation unit 34 sets defect area information indicating the position and size of one defect area as defect information (step 307). Subsequently, the defect information generation unit 34 determines whether there are other defect areas (step 308). If there are other defect areas, step 307 is repeated. If not, the defect information generation unit 34 passes the generated defect information on to the transmission/reception unit 31. The transmission/reception unit 31 transmits the defect information to the capture unit 20 (step 309). Subsequently, the transmission/reception unit 31 deletes this capture image from the buffer 32 (step 310).

Figure 9:
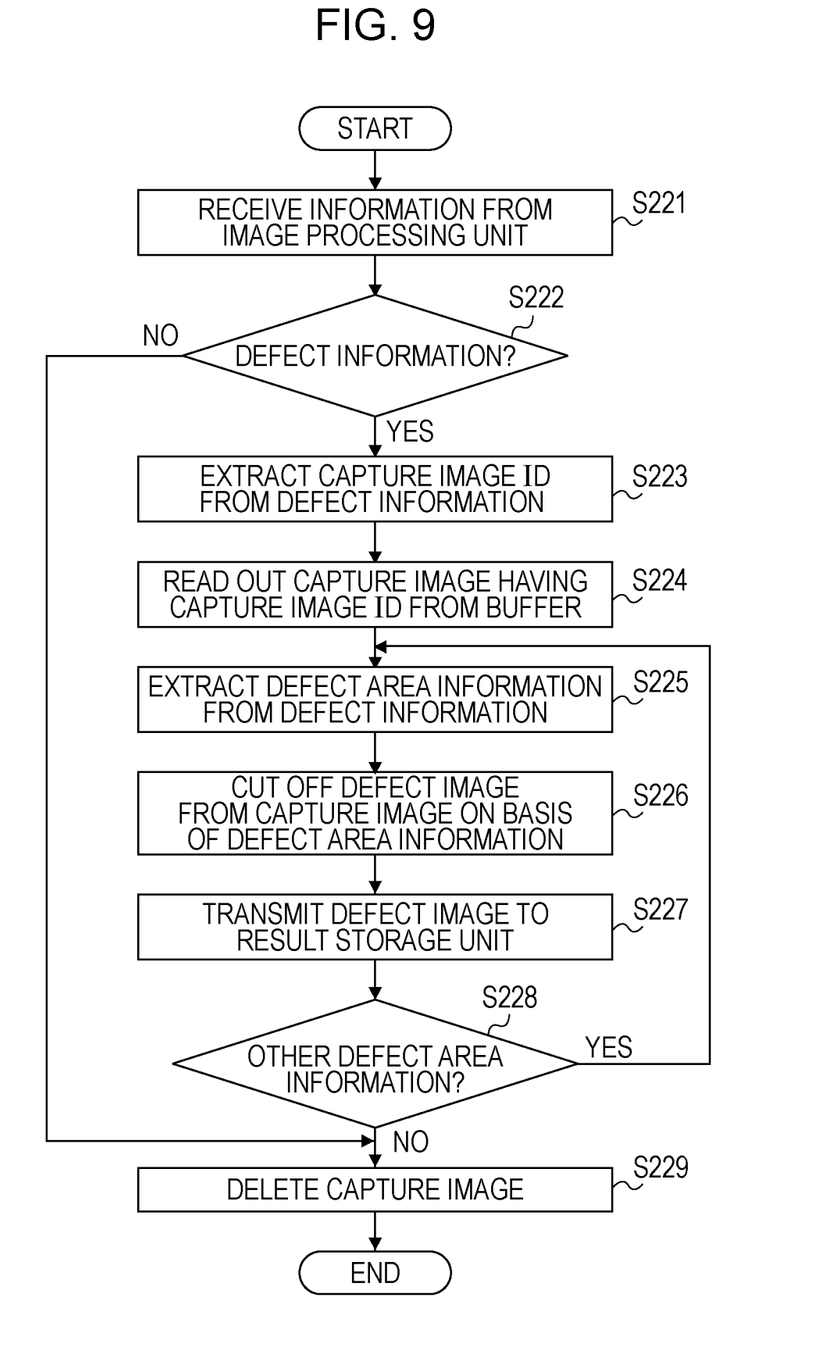
FIG. 9 is a flowchart showing an example of operations performed by the capture unit according to this embodiment that has received information from the image processing unit.

FIG. 9 is an example of operations performed by the capture unit 20 that has received information from the image processing unit 30. In the capture unit 20, first, the transmission/reception unit 23 receives information (step 221). Subsequently, the transmission/reception unit 23 determines whether the information is defect information (step 222).

If the transmission/reception unit 23 determines that the information is not defect information, that is, if the transmission/reception unit 23 determines that the information includes a capture image ID and information indicating that a capture image corresponding to the capture image ID has no defect, the transmission/reception unit 23 deletes the capture image corresponding to the capture image ID stored in the buffer 24 (step 229).

In contrast, if the transmission/reception unit 23 determines that the information is defect information, the transmission/reception unit 23 transmits the defect information to the image extraction unit 25. The image extraction unit 25 extracts a capture image ID from the defect information (step 223). Subsequently, the image extraction unit 25 reads out a capture image corresponding to the capture image ID from the buffer 24 (step 224). Subsequently, the image extraction unit 25 extracts one piece of defect area information from the defect information (step 225). Subsequently, the image extraction unit 25 cuts off, from the capture image, an image of a defect area identified by the defect area information, that is, a defect image (step 226). Subsequently, the image extraction unit 25 passes the cut-off defect image to the transmission unit 26. The transmission unit 26 transmits the defect image to the result storage unit 40 (step 227). Subsequently, the image extraction unit 25 determines whether there is other defect area information (step 228). If there is other defect area information, steps 225 to 227 are repeated. If not, the image extraction unit 25 provides notification to that effect to the transmission/reception unit 23. Subsequently, the transmission/reception unit 23 deletes the capture image corresponding to the capture image ID stored in the buffer 24 (step 229).

In these example operations, each time a defect image is cut off from a capture image in step 226, the defect image is transmitted to the result storage unit 40 in step 227. However, the image extraction unit 25 may retain the defect image cut off from the capture image in step 226 until the image extraction unit 25 determines in step 228 that there is no other defect area information and, after making such a determination, may collectively transmit the defect images to the result storage unit 40.

While defect information according to this embodiment includes a capture image ID and defect area information, defect information may include only one of these items.

For example, it is considered to include only defect area information in defect information. In this case, it is assumed that a capture image transmitted to the image processing unit 30 and a capture image stored in the buffer 24 are associated with each other using a method other than the method using a capture image ID. Specifically, the capture unit 20 transmits one capture image to the image processing unit 30 and as well as stores the capture image in the buffer 24, the image processing unit 30 processes the capture image and then transmits defect area information to the capture unit 20, the capture image is deleted from both the image processing unit 30 and buffer 24, and a subsequent capture image is handled. In this case, the capture unit 20 cuts off a defect image from the one capture image stored in the buffer 24 on the basis of the defect area information.

Also, it is considered to include only a capture image ID in defect information. Specifically, multiple capture images are transmitted to the image processing unit 30 and then stored in the buffer 24. Upon receipt of a capture image ID of a capture image including a defect image, the capture unit 20 selects a capture image having the received capture image ID from among the capture images stored in the buffer 24 and then transmits the capture image to the result storage unit 40. In this case, the capture unit 20 transmits the whole selected capture image including the defect image to the result storage unit 40 without cutting off the defect image from the capture image. In this case, if the size of each capture image is previously set to a small size, the communication load is not significantly increased even if a whole capture image is transmitted.

The embodiment of the present invention has heretofore been described in detail.

By performing the operations described in this embodiment, the problems with the related art are solved as follows.

Since the image processing unit 30 no longer transmits any defect image, the transmission bandwidth necessary for the image processing unit 30 may be small. Although the transmission bandwidth necessary for the capture unit 20 is increased, it is no problem because a unit such as a server is used as the capture unit 20 and thus the transmission bandwidth is increased more easily and at lower cost than that for the image processing unit 30.

The image processing unit 30 does not need to perform an extra process such as the compression of a defect image. Accordingly, the time that the image processing unit 30 can originally use to analyze an image will not be affected.

Also, the following advantages are obtained.

Since the process of extracting a defect image is also off-loaded from the image processing unit 30 and loaded on to the capture unit 20, the time that the image processing unit 30 can originally use to analyze an image is increased.

A memory or a disk of the capture unit 20 can be expanded more easily and at lower cost than those of the image processing unit 30. Accordingly, by including a large buffer in the capture unit 20, the amount of image processing performed by the entire system is increased.

While the capture unit 20 is realized by a server and the image processing unit 30 is realized by a blade server in this embodiment, the capture unit 20 may be realized by a general-purpose computer such as a personal computer (PC). Also, the image processing unit 30 may be realized by a general-purpose computer such as a PC including a cell accelerator board (CAB).

Assuming that the above-mentioned processes are performed by a general-purpose computer, a hardware configuration of the general-purpose computer will be described.

Figure 10:
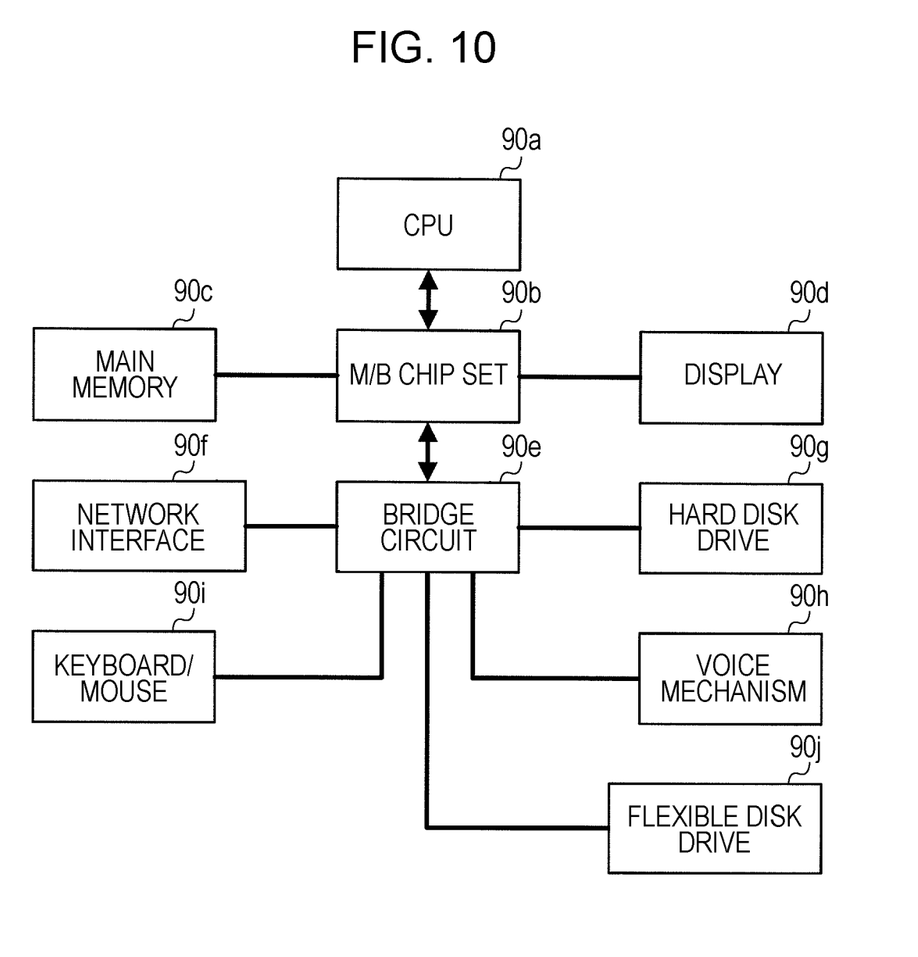
FIG. 10 is a diagram showing a hardware configuration of a computer to which this embodiment is applicable.

FIG. 10 is a diagram showing an example hardware configuration of such a computer. As shown in FIG. 10, the computer includes a central processing unit (CPU) 90*a* as a computation means, a main memory 90*c* coupled to the CPU 90*a* via an M/B (motherboard) chipset 90*b*, and a display 90*d* coupled to the CPU 90*a* via the M/B chip set 90*b*. Coupled to the M/B chipset 90*b* via a bridge circuit 90*e* are a network interface 90*f*, a hard disk drive (HDD) 90*g*, a voice mechanism 90*h*, a keyboard/mouse 90*i*, and a flexible disk drive 90*j*.

The above-mentioned components are coupled to one another via buses in FIG. 10. For example, the CPU 90*a* and M/B chip set 90*b* as well as the M/B chip set 90*b* and main memory 90*c* are coupled via a CPU bus. The M/B chip set 90*b* and display 90*d* may be coupled via an accelerated graphics port (AGP). If the display 90*d* includes a PCI Express-compliant video card, the M/B chip set 90*b* and this video card are coupled via a PCI Express (PCIe) bus. The network interface 90*f* is coupled to the bridge circuit 90*e* via, e.g., PCI Express. The hard disk drive 90*g* is coupled to the bridge circuit 90*e* via, e.g., serial AT attachment (ATA), parallel transfer ATA, or peripheral components interconnect (PCI). The keyboard/mouse 90*i* and flexible disk drive 90*j* are coupled to the bridge circuit 90*e* via universal serial buses (USB).

The present invention may be realized solely by hardware or software or may be realized by both hardware and software. In other words, the present invention may be realized by any of a computer, a data processing system, and a computer program. Such a computer program may be stored in a computer-readable medium and then provided. Among such computer-readable media are electronic media, magnetic media, optical media, electromagnetic media, infrared or semiconductor systems (devices), and propagation media. More specifically, computer-readable media include semiconductors or solid-state storage devices, magnetic tapes, detachable computer diskettes, random access memories (RAMs), read-only memories (ROMs), rigid magnetic disks, and optical disks. Among currently available optical disks are compact disc-read only memories (CD-ROMs), compact disc-read/write (CD-R/W), and digital versatile discs (DVDs).

While the present invention has been described using the embodiment thereof, the technical scope of the invention is not limited thereto. It will be apparent for those skilled in the art that various changes can be made to the embodiment or various substitutes therefor can be used without departing from the spirit and scope of the invention.

The invention claimed is:

1. A system for supporting discovery of a defect included in an inspection subject, comprising:
   an acquisition unit for acquiring a photographic image obtained by photographing the inspection subject;
   a determination unit coupled to the acquisition unit via a first communication line and configured to determine whether the photographic image obtained by the acquisition unit includes a defect image that is an image of an area including a defective portion of the inspection subject; and
   a storage unit coupled to the acquisition unit via a second communication line and configured to, if the determination unit determines that the photographic image includes the defect image, store the defect image, wherein
   the acquisition unit transmits the photographic image to the determination unit via the first communication line as well as stores the photographic image in a memory thereof, and if the acquisition unit receives image identification information for identifying the defect image from the determination unit via the first communication line, the acquisition unit transmits the defect image that is included in the photographic image stored in the memory and is identified by the image identification information, to the storage unit via the second communication line.

2. The system according to claim 1, wherein
   the image identification information includes at least one of an identification number of the photographic image, a number of the defective portions, and defect area information including a coordinate and an area of the defective portion.

3. The system according to claim 1, wherein
   the acquisition unit cuts off the defect image from the photographic image stored in the memory and transmits the cut-off defect image to the storage unit.

4. The system according to claim 3, wherein
   if the acquisition unit receives, as the image identification information, area identification information for identifying an area occupied by the defect image in the photographic image stored in the memory, the acquisition unit cuts off, as the defect image, an area identified by the area identification information from the photographic image.

5. The system according to claim 1, wherein
if the acquisition unit receives, from the determination unit, information indicating that the photographic image stored in the memory does not include the defect image, the acquisition unit deletes the photographic image from the memory.

6. The system according to claim 1, wherein
the photographic image includes a plurality of fragments, and
if the determination unit determines that at least one of the fragments included in the photographic image includes the defect image, the acquisition unit transmits, to the storage unit, the at least one fragment including the defect image among the fragments included in the photographic image stored in the memory.

7. The system according to claim 6, wherein
if the acquisition unit receives, as the image identification information, fragment identification information for identifying the fragment including the defect image among the fragments included in the photographic image stored in the memory, from the determination unit, the acquisition unit transmits the at least one fragment identified by the fragment identification information among the fragments, to the storage unit.

8. The system according to claim 1, wherein
the photographic image includes a plurality of fragments, and
if the acquisition unit receives, from the determination unit, information indicating that a particular fragment among the fragments included in the photographic image stored in the memory does not include the defect image, the acquisition unit deletes the particular fragment from the memory.

9. The system according to claim 1, wherein
if the determination unit determines that the photographic image includes the defect image, the determination unit deletes the defect image without transmitting the defect image to the acquisition unit.

10. The system according to claim 1, wherein
the second communication line is larger in bandwidth than the first communication line.

11. A method for supporting discovery of a defect included in an inspection subject, comprising the steps of:
acquiring, from a photographing unit, a photographic image obtained by photographing the inspection subject using the photographing unit, by using an acquisition unit;
transmitting the photographic image to a determination unit via a first communication line by using the acquisition unit;
storing the photographic image in a memory of the acquisition unit by using the acquisition unit;
determining whether the photographic image received from the acquisition unit via the first communication line includes a defect image that is an image of an area including a defective portion of the inspection subject, by using the determination unit;
if the determination unit determines that the photographic image includes the defect image, transmitting image identification information for identifying the defect image to the acquisition unit via the first communication line, by using the determination unit; and
transmitting the defect image that is included in the photographic image stored in the memory and is identified by the image identification information, to a storage unit via the second communication line by using the acquisition unit.

12. A method for supporting discovery of a defect included in an inspection subject, comprising the steps of:
acquiring, from a photographing unit, a plurality of fragments of a photographic image obtained by photographing the inspection subject using the photographing unit, by using an acquisition unit;
transmitting the fragments to a determination unit via a first communication line by using the acquisition unit;
storing the fragments in a memory of the acquisition unit by using the acquisition unit;
determining whether at least one of the fragments received from the acquisition unit via the first communication line includes a defect image that is an image of an area including a defective portion of the inspection subject, by using the determination unit;
if the determination unit determines that at least one of the fragments includes the defect image, transmitting fragment identification information for identifying the at least one fragment including the defect image among the fragments stored in the memory and area identification information for identifying an area occupied by the at least one defect image in the fragment to the acquisition unit via the first communication line, by using the determination unit;
cutting off, as the defect image, an area that is included in the at least one fragment identified by the fragment identification information among the fragments stored in the memory and is identified by the area identification information, by using the acquisition unit; and
transmitting the cut-off defect image to a storage unit by using the acquisition unit.

* * * * *